US008945914B1

(12) United States Patent
Schaff et al.

(10) Patent No.: US 8,945,914 B1
(45) Date of Patent: Feb. 3, 2015

(54) DEVICES, SYSTEMS, AND METHODS FOR CONDUCTING SANDWICH ASSAYS USING SEDIMENTATION

(75) Inventors: Ulrich Y. Schaff, Davis, CA (US); Gregory J. Sommer, Livermore, CA (US); Anup K. Singh, Danville, CA (US); Anson V. Hatch, Tracy, CA (US)

(73) Assignee: Sandia Corporation, Albuquerque, NM (US)

( * ) Notice: Subject to any disclaimer, the term of this patent is extended or adjusted under 35 U.S.C. 154(b) by 495 days.

(21) Appl. No.: 12/891,977

(22) Filed: Sep. 28, 2010

Related U.S. Application Data

(60) Provisional application No. 61/362,398, filed on Jul. 8, 2010, provisional application No. 61/362,407, filed on Jul. 8, 2010.

(51) Int. Cl.
*C12M 1/34* (2006.01)
*G01N 15/04* (2006.01)
*B01L 3/00* (2006.01)

(52) U.S. Cl.
CPC .......... *G01N 15/042* (2013.01); *B01L 3/50273* (2013.01); *B01L 3/5027* (2013.01); *B01L 2400/0409* (2013.01)
USPC .................. 435/288.7; 435/286.5; 435/287.1; 435/288.6; 427/2.11; 427/2.3

(58) Field of Classification Search
USPC ...................... 435/288.7, 286.5, 287.1, 288.6; 427/2.11, 2.3
See application file for complete search history.

(56) References Cited

U.S. PATENT DOCUMENTS

| 3,376,083 | A |   | 4/1968  | Everhardus |
|-----------|---|---|---------|------------|
| 3,555,284 | A |   | 1/1971  | Anderson |
| 3,744,974 | A |   | 7/1973  | Maddox |
| 3,844,341 | A |   | 10/1974 | Bimshas, Jr. et al. |
| 4,125,375 | A | * | 11/1978 | Hunter .......................... 436/518 |
| 4,156,570 | A |   | 5/1979  | Wardlaw .......................... 356/36 |
| 4,164,690 | A |   | 8/1979  | Muller et al. |
| 4,282,464 | A |   | 8/1981  | Uzuka |

(Continued)

FOREIGN PATENT DOCUMENTS

| JP | 0407169887 A | 7/1995 |
|----|--------------|--------|
| JP | 2000-054978  | 2/2000 |

(Continued)

OTHER PUBLICATIONS

Abi-Samira, K. et al., "Infrared Controlled Waxes for Liquid-Handling and Storage on a CD-Microfluidic Platform", The Royal Society of Chemistry, Lab Chip, 2011, pp. 723-726.

(Continued)

*Primary Examiner* — Melanie Y Brown
(74) *Attorney, Agent, or Firm* — Dorsey & Whitney, LLP

(57) ABSTRACT

Embodiments of the present invention are directed toward devices, systems, and method for conducting sandwich assays using sedimentation. In one example, a method includes generating complexes on a plurality of beads in a fluid sample, individual ones of the complexes comprising a capture agent, a target analyte, and a labeling agent. The plurality of beads including the complexes may be transported through a density media, wherein the density media has a density lower than a density of the beads and higher than a density of the fluid sample, and wherein the transporting occurs, at least in part, by sedimentation. Signal may be detected from the labeling agents of the complexes.

22 Claims, 8 Drawing Sheets

Before Sedimentation    After Sedimentation

(56) References Cited

U.S. PATENT DOCUMENTS

| | | | |
|---|---|---|---|
| 4,380,355 A | 4/1983 | Beardmore | |
| 4,554,071 A | 11/1985 | Ruijten et al. | |
| 4,656,143 A | 4/1987 | Baker et al. | |
| 4,683,579 A | 7/1987 | Wardlaw | 377/11 |
| 4,844,818 A | 7/1989 | Smith | |
| 5,000,254 A | 3/1991 | Williams | |
| 5,197,858 A | 3/1993 | Cheng | |
| 5,279,936 A | 1/1994 | Vorpahl | |
| 5,296,775 A | 3/1994 | Cronin et al. | |
| 5,297,623 A | 3/1994 | Ogushi et al. | |
| 5,335,143 A | 8/1994 | Maling, Jr. et al. | |
| 5,583,746 A | 12/1996 | Wang | |
| 5,616,974 A | 4/1997 | Yamada | |
| 5,635,362 A | 6/1997 | Levine et al. | |
| 5,705,628 A | 1/1998 | Hawkins | |
| 5,727,928 A | 3/1998 | Brown | |
| 5,736,787 A | 4/1998 | Larimer | |
| 5,794,687 A | 8/1998 | Webster et al. | |
| 5,882,903 A | 3/1999 | Andrevski et al. | |
| 5,947,659 A | 9/1999 | Mays | |
| 5,957,659 A | 9/1999 | Amou et al. | |
| 5,963,887 A | 10/1999 | Giorgio | |
| 5,979,541 A | 11/1999 | Saito | |
| 6,050,326 A | 4/2000 | Evans et al. | |
| 6,078,468 A | 6/2000 | Fiske | |
| 6,153,148 A | 11/2000 | Thomas | 422/72 |
| 6,175,495 B1 | 1/2001 | Batchelder | |
| 6,194,798 B1 | 2/2001 | Lopatinsky | |
| 6,249,071 B1 | 6/2001 | Lopatinsky et al. | |
| 6,319,469 B1 | 11/2001 | Mian et al. | 422/64 |
| 6,356,435 B1 | 3/2002 | Davis et al. | |
| 6,392,720 B1 | 5/2002 | Kim | |
| 6,457,955 B1 | 10/2002 | Cheng | |
| 6,525,938 B1 | 2/2003 | Chen | |
| 6,545,438 B1 | 4/2003 | Mays, II | |
| 6,619,385 B2 | 9/2003 | Watanabe et al. | |
| 6,623,860 B2 | 9/2003 | Hu et al. | |
| 6,659,169 B1 | 12/2003 | Lopatinsky et al. | |
| 6,664,673 B2 | 12/2003 | Askhatov et al. | |
| 6,860,323 B2 | 3/2005 | Cheng | |
| 6,873,069 B1 | 3/2005 | Odagiri et al. | |
| 6,879,120 B2 | 4/2005 | Xi | |
| 6,887,384 B1 | 5/2005 | Frechet et al. | |
| 6,955,215 B2 | 10/2005 | Al-Garni et al. | |
| 7,021,894 B2 | 4/2006 | Lopatinsky et al. | |
| 7,033,747 B2 | 4/2006 | Gordon | |
| 7,035,102 B2 | 4/2006 | Holmes | |
| 7,044,202 B2 | 5/2006 | Lopatinsky et al. | |
| 7,055,581 B1 | 6/2006 | Roy | |
| 7,071,587 B2 | 7/2006 | Lopatinsky et al. | |
| 7,134,839 B2 | 11/2006 | Horng et al. | |
| 7,136,285 B1 | 11/2006 | Herbert | |
| 7,157,049 B2 | 1/2007 | Valencia et al. | 422/68.1 |
| 7,165,413 B2 | 1/2007 | Symons | |
| 7,165,938 B2 | 1/2007 | Lee et al. | |
| 7,265,975 B2 | 9/2007 | Tsai | |
| 7,267,526 B2 | 9/2007 | Hsu et al. | |
| 7,273,091 B2 | 9/2007 | Bahl et al. | |
| 7,304,845 B2 | 12/2007 | Xia | |
| 7,324,339 B2 | 1/2008 | Foster, Sr. | |
| 7,349,212 B2 | 3/2008 | Xia | |
| 7,381,027 B2 | 6/2008 | Kaneko et al. | |
| 7,458,413 B2 | 12/2008 | Mok | |
| 7,481,263 B2 | 1/2009 | Breier et al. | |
| 7,520,314 B2 | 4/2009 | Hwang et al. | |
| 7,543,457 B2 | 6/2009 | Crocker et al. | |
| 7,670,102 B2 | 3/2010 | Chang et al. | |
| 7,695,256 B2 | 4/2010 | Horng et al. | |
| 7,758,810 B2 | 7/2010 | Lee et al. | 422/72 |
| 7,836,939 B2 | 11/2010 | Zimmerman et al. | |
| 7,896,611 B2 | 3/2011 | Khanna et al. | |
| 7,900,690 B2 | 3/2011 | Hawwa et al. | |
| 7,905,712 B2 | 3/2011 | Huang | |
| 7,911,791 B2 | 3/2011 | Refai-Ahmed et al. | |
| 8,337,775 B2 | 12/2012 | Pugia et al. | |
| 2001/0055812 A1* | 12/2001 | Mian et al. | 436/45 |
| 2002/0090307 A1 | 7/2002 | Cheng | |
| 2002/0098535 A1 | 7/2002 | Wang et al. | |
| 2002/0137068 A1 | 9/2002 | Haugland et al. | |
| 2002/0151043 A1* | 10/2002 | Gordon | 435/287.2 |
| 2002/0153251 A1 | 10/2002 | Sassi et al. | |
| 2002/0164659 A1* | 11/2002 | Rao et al. | 435/7.5 |
| 2002/0170825 A1 | 11/2002 | Lee et al. | |
| 2003/0013203 A1 | 1/2003 | Jedrzejewski et al. | |
| 2003/0124719 A1 | 7/2003 | Woodside | |
| 2003/0203504 A1 | 10/2003 | Hefti | |
| 2003/0221963 A1 | 12/2003 | Bjellqvist et al. | |
| 2004/0035556 A1 | 2/2004 | Jean | |
| 2004/0072278 A1 | 4/2004 | Chou et al. | |
| 2004/0109291 A1 | 6/2004 | Kannmacher et al. | |
| 2004/0114327 A1 | 6/2004 | Sri-Jayantha et al. | |
| 2004/0119354 A1 | 6/2004 | Takada | |
| 2005/0002163 A1 | 1/2005 | Lopatinsky et al. | |
| 2005/0087445 A1 | 4/2005 | Speicher et al. | |
| 2005/0195573 A1 | 9/2005 | Huang | |
| 2005/0215410 A1* | 9/2005 | Merino et al. | 494/37 |
| 2005/0274490 A1 | 12/2005 | Larson | |
| 2006/0007656 A1 | 1/2006 | Symons | |
| 2006/0021735 A1 | 2/2006 | Lopatinsky et al. | |
| 2006/0171654 A1 | 8/2006 | Hawkins et al. | |
| 2006/0191792 A1 | 8/2006 | Herr et al. | |
| 2007/0000268 A1 | 1/2007 | Crocker et al. | |
| 2007/0041158 A1 | 2/2007 | Hornung | |
| 2007/0231419 A1 | 10/2007 | Pelcz et al. | |
| 2008/0069706 A1 | 3/2008 | Huang | |
| 2008/0149484 A1 | 6/2008 | Tolley et al. | |
| 2009/0004059 A1* | 1/2009 | Pugia et al. | 422/68.1 |
| 2009/0069554 A1 | 3/2009 | Finne | |
| 2009/0145584 A1 | 6/2009 | Walsh et al. | |
| 2009/0166004 A1 | 7/2009 | Lai et al. | |
| 2009/0209402 A1 | 8/2009 | Andersson | |
| 2010/0068754 A1 | 3/2010 | Kirakossian | |
| 2010/0120596 A1 | 5/2010 | Froman et al. | |
| 2010/0151560 A1 | 6/2010 | Wo et al. | |
| 2010/0177480 A1 | 7/2010 | Koplow | |
| 2010/0328887 A1 | 12/2010 | Refai-Ahmed et al. | |
| 2011/0103011 A1 | 5/2011 | Koplow | |

FOREIGN PATENT DOCUMENTS

| | | |
|---|---|---|
| JP | 02000341902 A | 12/2000 |
| JP | 2006-037918 | 2/2006 |
| WO | 2000/054978 | 2/2000 |
| WO | WO01/68225 A1 | 9/2001 |
| WO | WO-2008/143578 | 11/2008 |
| WO | WO-2009/098237 | 8/2009 |
| WO | WO2010/016963 A1 | 2/2010 |

OTHER PUBLICATIONS

Albrecht, J W. et al., "Micro Free-Flow IEF Enhanced by Active Cooling and Functionalized Gels", Electrophoresis, 2006, pp. 4960-4969, vol. 27.

Amersham, M. "Percoll: Methodology and Applications", 2001, pp. 1-84.

Baldwin, Robert L., "How Hofmeister Ion Interactions Affect Protein Stability," Biophysical Journal, vol. 71, Oct. 1996, pp. 2056-2063.

Boyko, M. et al., "Cell-Free DNA—A Marker to Predict Ischemic Brain Damage in a Rat Stroke Experimental Model," J. Neurosurg. Anesthesiol. vol. 23, No. 3, Jul 2011, pp. 222-228.

Cabrera, C R. et al., "Formation of Natural pH Gradients in a Microfluidic Device under Flow Conditions: Model and Experimental Validation", Analytical Chemistry, 2001, pp. 658-666, vol. 73.

Carney, J. "Rapid Diagnostic Tests Employing Latex Particles," Analytical Proceedings, Apr. 1990, pp. 27:99-100.

Cui, Huanchun et al., "Multistage Isoelectric Focusing in a Polymeric Microfluidic Chip", Analytical Chemistry, Dec. 15, 2005, pp. 7878-7886, vol. 77, No. 24.

Curtis, R.A. et al., "A Molecular Approach to Bioseparations: Protein-Protein and Protein-Salt Interactions," Chemical Engineering Science, 2006, vol. 61, pp. 907-923.

(56) References Cited

OTHER PUBLICATIONS

Czeiger, D. et al., "Measurement of Circulating Cell-Free DNA Levels by a New Simple Fluorescent Test in Patients with Primary Colorectal Cancer," Am. J. Clin. Pathol., 2011, vol. 135, pp. 264-270.
Das, C., et al. "Effects of Separation Length and Voltage on Isoelectric Focusing in a Plastic Microfluidic Device", Electrophoresis, 2006, pp. 3619-3626, vol. 27.
Folgea, D. et al., "Detecting Single Stranded DNA with a Solid State Nanopore", Nano Letters, 2005, vol. 5, No. 10, pp. 1905-1909.
Glorikian, H. et al., "Overview of Microfluidic Applications IN IVDS", DX Direction 1, 2010, pp. 12-16.
Golorkian, H. et al., "Smart-Consumables Product Development Strategy: Implications for Molecular Diagnostics", DX Direction, 2010, 12-16.
Goldshtein, H., et al., "A Rapid Direct Fluorescent Assay for Cell-Free DNA Quantification in Biological Fluids," Annals of Clinical Biochemistry, vol. 46, pp. 488-494, 2009.
Gorg, A. et al., "Recent Developments in Two-Dimensional Gel Electrophoresis with Immobilized pH Gradients: Wide pH Gradients Up to pH 12, Longer Separation Distances and Simplified Procedures", Electrophoresis, vol. 20, 1999, pp. 712-717.
Gorg, A. et al., "The Current State of Two-Dimensional Electrophoresis with Immobilized pH Gradients", Electrophoresis, vol. 21, 2000, pp. 1037-1053.
Hatch, A V. et al., "Integrated Preconcentration SDS-PAGE of Proteins in Microchips Using Photopatterned Cross-Linked Polyacrylamide Gels", Analytical Chemistry, vol. 78, 2006, pp. 4976-4984.
Herr, A E. et al., "Microfluidic Immunoassays as Rapid Saliva-Based Clinical Diagnostics", PNAS, vol. 104, No. 13, 2007, pp. 5268-5273.
Herr, A E. et al., "On-Chip Coupling of Isoelectric Focusing and Free Solution Electrophoresis for Multidimensional Separations", Analytical Chemistry, vol. 75, 2003, pp. 1180-1187.
Holmes, D., et al., "Leukocyte Analysis and Differntiation Using High Speed Microfluidic Singe Cell Impedance Cytometry", Lab Chip 9, 2009, pp. 2881-2889.
Huang, T et al., "Microfabrication of a Tapered Channel for Isoelectric Focusing with Thermally Generated pH Gradient", Electrophoresis, vol. 23, 2002, pp. 3504-3510.
International Search Report dated Dec. 24, 2009 for PCT/US2009/044550.
International Search Report dated Mar. 1, 2012 for PCT/US2012/027299.
Invitrogen Life Technologies, Instructional Manual, ZOOM IEF Fractionator, Cat. Nos. ZF10001 & ZF10002, Version C, Jul. 2004, pp. 1-64.
Lee, B.S., et al., "A Fully Automated Immunoassay From Whole Bloon n a Disc"; Lab Chip 9, 2009, pp. 1548-1555.
Lim, C.T. and Zhang, Y., "Bead-Based Microfluidic Immunoassays: The Next Generation", Biosens. Bioelectron. 22, 2007I, pp. 1197-1204.
Lim, P., et al., "Rapid isoelectric trapping in a micropreparative-scale multicompartment electrolyzer", Electrophoresis, 2007. vol. 28, pp. 1851-1859.
Lo, C T. et al., "Photoploymerized Diffusion-Defined Ployacrylamide Gradient Gels for On-Chip Protein Sizing", The Royal Society of Chemistry, Lab on a Chip, vol. 8, No. 8, 2008, pp. 1273-1279.
Lo, Y. et al., "Plasma DNA as a Prognostic Marker in Trauma Patients", Clinical Chemistry 46:3, 2009, pp. 319-323.
Long, et al., "Integration of nanoporous membranes for sample filtration/preconcentration in microchip electrophoresis", Electrophoresis, 2004, pp. 4927-4934, vol. 27.
Madou, M., et al., "Lab on a CD"; Annu. Rev. Biomed. Eng. 8, 2006, pp. 601-628.
Maes, M., et al., "Comparison of Sample Fixation and The Use of LDS-751 or Anti-CD45 for Leukocyte Identification in Mouse Whole Blood for Flow Cytometry", Journal of Immunogical Methods, 2007, p. 1-13.

Min, J. et al., "Functional Integration of DNA Purification and Concentration into a Real Time Micro-PCR Chip," The Royal Society of Chemistry; Lab Chip, 2011, pp. 259-265.
O'Farrell, P. H., "High Resolution Two-Dimensional Electrophoresis of Proteins", The Journal of Biological Chemistry, vol. 250, No. 9, 1975, pp. 4007-4021.
Ogle, et al., "Preparative-scale isoelectric trapping separations using a modified Gradiflow Unit", Journal of Chromatorgraphy A, 2002, vol. 979, pp. 155-161.
Price, C.P., et al., "Light-Scattering Immunoassay," Principles and Practice Immunoassay (Second Edition), 1997, Chap. 18, pp. 445-480.
Rhodes, A., et al., "Plasma DNA Concentration as a Predictor of Mortality and Sepsis in Critically Ill Patients," Critical Care, 2006, pp. 1-7.
Rider, T, et al., "AB Cell-Based Sensor for Rapid Identification of Pathogens"; wwwsciencemag.org; Science vol. 301; 2003, pp. 213-215.
Riegger, L., et al., "Read-Out Concepts for Multiplexed Bead-Based Flourescence Immunoassays on Centrifugal Microfluidic Platforms," Sensors and Actuators A 125, 2006, pp. 455-462.
Righetti, P G. "The Alpher, Bethe, and Gamow of IEF, the Alpha-Centaury of Electrokinetic Methodologies, Part II: Immobilized pH Gradients", Electrophoresis, 2007, pp. 545-555, vol. 28.
Righetti, P G. "The Alpher, Bethe, Gamow of Isoelectric Focusing, the Alpha-Centaury of Electrokinetic Methodologies. Part 1", Electrophoresis, 2006, pp. 923-938, vol. 27.
Satomi, T. et. al., "Design Optimization of Spirally Grooved Thrust Air Gearings for Polygon Mirrow Laser Scanners", The Japan Society of Mechanical Engineers, 1993, Series C., vol. 36(3), pp. 393-399.
Schaff, U.Y., et al., "Whole Blood Immunoassay Based on Centrifugal Bead Sedimentation," Clinical Chemistry, 2011, vol. 57:5, pp. 753-761.
Sommer, G. J. et al., "On-Chip Isoelectric Focusing Using Photopolymerized Immobilized pH Gradients", Analytical Chemistry, 2008, pp. 3327-3333, vol. 80.
Tan, W. et al., "Miniaturized Capillary Isoelectric Focusing in Plastic Microfluidic Devices", Electrophoresis, 2002, pp. 3638-3645, vol. 23.
Zhang, L., et al., "A New Biodosimetric Method: Branched DNA-Based Quantitative Detection of B1 DNA in Mouse Plasma," The British Journal of Radiology, Aug. 3, 2010, pp. 694-701.
Ziegler, A. et al., "Circulating DNA: A New Diagnostic Gold Mine?" Cancer Treatment Reviews, 2002, vol. 28, pp. 255-271.
Zilberstein, G. et al., "Parallel Isoelectric Focusing Chip", Proteomics, 2004, pp. 2533-2540, vol. 4.
Zilberstein, G. et al., "Parallel isoelectric focusing II", Electrophoresis 2004, vol. 25, pp. 3643-3651.
Zilberstein, G. et al., "Parallel processing in the isoelectric focusing chip", Electrophoresis, 2003, vol. 24, pp. 3735-3744.
Zuo, X; Speicher, D.W.; "A Method for Global Analysis of Complex Proteoms Using Sample Prefactionation by Solution Isoelectrofocusing Prior to Two-Dimensional Electrophoresis", Analytical Biochemistry, 2000, vol. 284, pp. 266-278.
Ahanotu, et al., "Staphylococcal Enterotoxin B as a Biological Weapon: Recognition, Management, and Surveillance of Staphylococcal Enterotoxin", Applied Biosafety; vol. 11 (3), 2006, 120-126.
Amukele, et al., "Ricin A-chain activity on stem-loop and unstructured DNA substrates.", Biochemistry; vol. 44(11), Mar. 25, 2005, 4416-4425.
Andersson, et al., "Parallel nanoliter microfluidic analysis system", Clinical Chemistry, 2007.
Berry, Scott M., "One-step Purification of Nucleic Acid for Gene Expression Analysis via Immiscible Filtration Assisted by Surface Tension", Lap Chip, May 21, 2011.
Brigotti, et al., "Shiga toxin 1 acting on DNA in vitro is a heat-stable enzyme not requiring proteolytic activation", Biochimie Journal; 86(45), 2004, 305-309.

(56) References Cited

OTHER PUBLICATIONS

Endo, et al., "RNA N-Glycosidase Activity of Ricin A-chain. Mechanism of Action of the Toxic Lectin Ricin on Eukaryotic Ribosomes", The Journal of Biological Chemistry, vol. 262, No. 17, Jun. 15, 1987, 8128-8130.

Gorkin, et al., "Centrifugal microfluidics for biomedical applications", www.rsc.org/loc; Lab on a Chip, May 2010, 1758-1773.

Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.

Huang, et al., "The Primary Structure of Staphylococcal Enterotoxin B. III. The Cyanogen Bromide Peptides of Reduced and Aminoethylated Enterotoxin B, and The Complete Amino Acid Sequence.", The Journal of Biological Chemistry vol. 245 No. 14, Jul. 25, 1970, 3518-3525.

International Search Report and Written Opinion dated Jun. 28, 2013 for PCT/US2013/032349.

Lee, et al., "Fully integrated lab-on-a-disc for simultaneous analysis of biochemistry and immunoassay from whole blood", Lab Chip, 2011.

Saukkonen, et al., "Cell-Free Plasma DNA as a Predictor of Outcome in Severe Sepsis and Septic Shock", Clinical Chemistry; vol. 54:6, 2008, 1000-1007.

Schembri, et al., "Portable Simultaneous Multiple Analyte Whole-Blood Analyzer for Point-of-Care Testing", Clinical Chemistry 38/9, 1992, 1665-1670.

Schneider, et al., "Characterization of EBV-Genome Negative "Null" and "T" Cell Lines Derived From Children With Acute Lymphoblastic Leukemia and Leukemic Transformed Non-Hodgkin Lymphoma", May 15, 1977, 621-626.

Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.

Todd H. Rider et al. "*A B Cell-Based Sensor for Rapid Identification of Pathogens*"; www.sciencemag.org; Science vol. 301; pp. 213-215 (2003).

Madou, M., et al, "*Lab on a CD*"; Annu Rev Biomed Eng 8, 601-628 (2006).

Lim, C.T. & Zhang. Y. "*Bead-Based Microfluidic Imunoassays: The Next Generation*"; Biosens Bioelectron 22, 1197-1204(2007).

Melissa L. Maes et al. "Comparison of Sample Fixation and the Use of LDS-751 or Anti-CD45 for Leukocyte Identification in Mouse Whole Blood for Flow Cytometry"; Journal of Immunological Methods, pp. 10-13 (2007).

Holmes, D et al; "Leukocyte Analysis and Differentiation Using High Speed Microfluidic Single Cell Impedance Cytometry"; Lab Chip 9; pp. 2881-2889 (2009).

Lee, B.S. et al. "*A Fully Automated Immunoassay From Whole Blood on a Disc*"; Lab Chip 9. pp. 1548-1555 (2009).

Golorikian. H., Zalesk, T. & Clancy, B. "*Overview of Microfluidic Applications in IVDS*". DX Direction 1. pp. 12-16 (2010).

\* cited by examiner

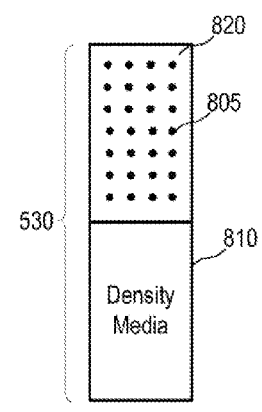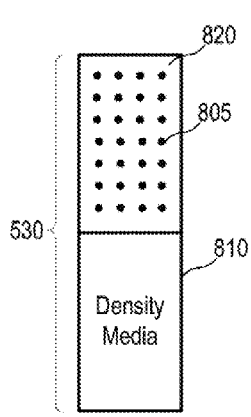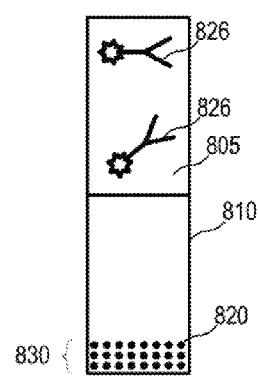
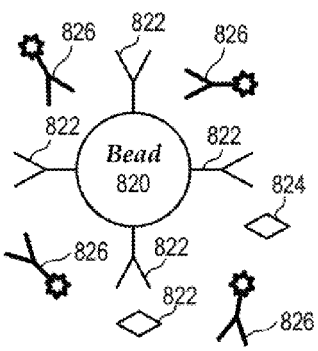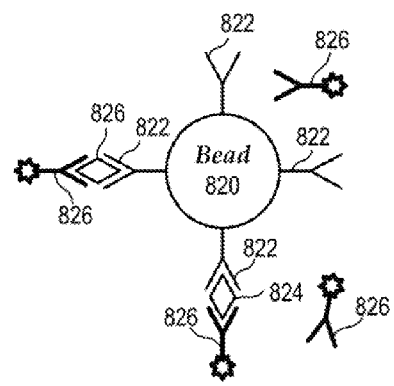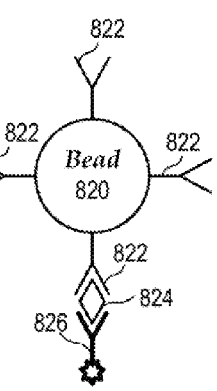
Figure 8                Figure 9                Figure 10

US 8,945,914 B1

DEVICES, SYSTEMS, AND METHODS FOR CONDUCTING SANDWICH ASSAYS USING SEDIMENTATION

CROSS-REFERENCE TO RELATED APPLICATION(S)

This application claims the benefit of the earlier filing dates of U.S. Provisional Applications 61/362,398 filed Jul. 8, 2010 and 61/362,407 filed Jul. 8, 2010, which provisional applications are both hereby incorporated by reference, in their entirety, for any purpose.

STATEMENT REGARDING RESEARCH & DEVELOPMENT

Described examples were made with Government support under Government Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

TECHNICAL FIELD

Embodiments of the invention relate generally to centrifugal systems and examples include methods, systems, and apparatus employing centrifugal forces for conducting a sandwich assay.

BACKGROUND

Sandwich assays generally proceed by adsorbing a target analyte onto a surface coated with a capture agent. The target analyte is then detected using a detection agent that also binds to the target analyte at a different site than the capture agent. Signal from the detection agent is used to detect the target analyte. FIGS. 1-3 are schematic illustrations of steps of a conventional sandwich assay.

FIG. 1 is a schematic illustration of a sample mixing step of a sandwich assay. A substrate 105 includes a number of capture agents 110 on a surface. A fluid sample including detection agents 112 and target analyte 114 is introduced to the surface.

FIG. 2 is a schematic illustration of an incubation step of a sandwich assay. The target analyte 114 binds to the capture agent 112. The detection agent 112 also binds to the target analyte 114. In this manner, complexes including a capture agent 110, a target analyte 114, and a capture agent 112 may be formed on the substrate 105. As shown in FIG. 2, some free detection agent 112 remains in the fluid sample and is not involved in a complex. The free detection agent 112 is not representative of the presence of target analyte, because it is not bound to target analyte. That is, the unbound detection agent may generate a false positive signal for presence of the target analyte. Accordingly, the signal from the free detection agent may obscure accurate detection. Accordingly, multiple wash steps are performed to rinse away the free detection agent, leaving only complexed detection agents bound to target analyte remaining on the substrate 105.

FIG. 3 is a schematic illustration of an amplification step of a sandwich assay. The detectable signal from the detection agent 112 bound to the substrate 105 may be too low for accurate detection. For example, the complexed detection agent 112 may be spread across too large an area of the substrate 105 to generate sufficient signal for detection. Accordingly, additional labeling agents 120 may be added and may bind to the complexes to increase the amount of signal generated by the complexes.

An example of a sandwich assay is the classical ELISA technique (enzyme linked immunosorbant assay). In ELISA, the capture and detection agents include antibodies and the target analyte is typically a protein.

Rather than a flat surface as shown in FIGS. 1-3, the surfaces of beads may be used to conduct a sandwich assay, with similar sample mixing, incubation, wash, and amplification steps.

Microfluidic systems, including "lab on a chip" or "lab on a disk" systems continue to be in development. See, Lee, B. S., et. al., "A fully automated immunoassay from whole blood on a disc," *Lab Chip* 9, 1548-1555 (2009) and Madou, M. et. al., "Lab on a CD," *Annu. Rev. Biomed. Engr.* 8, 601-628 (2006), which articles are hereby incorporated by reference in their entirety for any purpose.

BRIEF DESCRIPTION OF THE DRAWINGS

FIG. 8 is a schematic illustration of a detection region containing a sample fluid and a density media in accordance with an embodiment of the present invention.

FIG. 9 is a schematic illustration of the detection region of FIG. 8 following an incubation period in accordance with an embodiment of the present invention.

FIG. 10 is a schematic illustration of the detection region of FIG. 9 following transport of beads through the density media in accordance with an embodiment of the present invention.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Embodiments of the present invention are directed toward systems, apparatus, and methods for conducting a sandwich assay using sedimentation. Although examples are described below with reference to immunoassays, gene expression assays, and whole blood assays, and example capture agents, detection agents, and target analytes may be specified, it is to be understood that other sandwich assays may be carried out using embodiments of the present invention.

Figure 1:
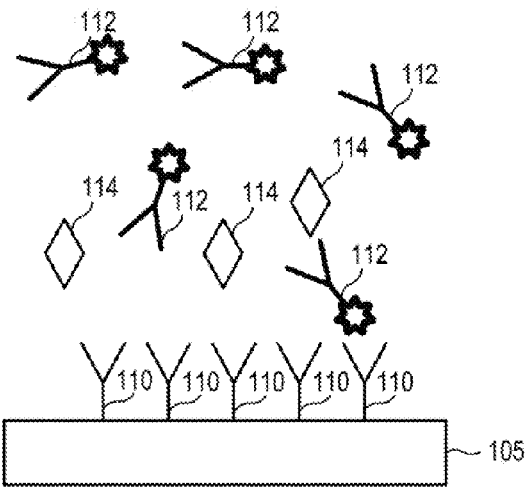
FIG. 1 is a schematic illustration of a sample mixing step of a sandwich assay as known in the art.
Figure 2:
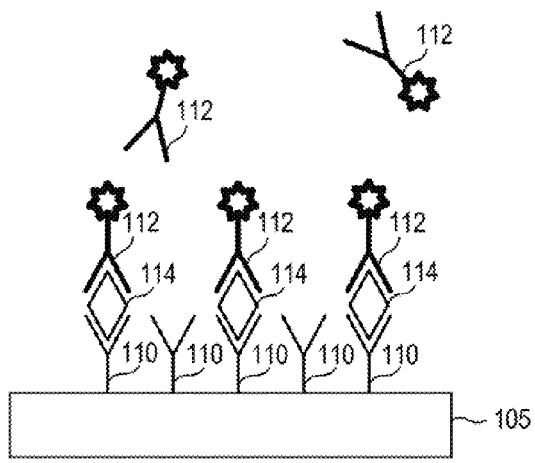
FIG. 2 is a schematic illustration of an incubation step of a sandwich assay as known in the art.
Figure 3:
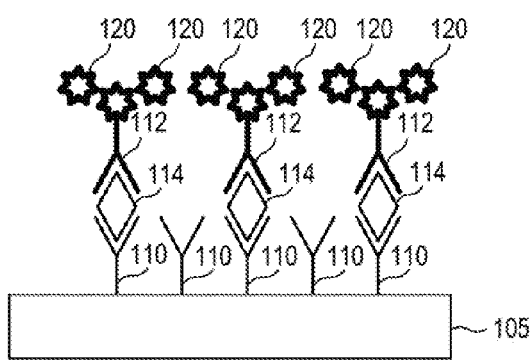
FIG. 3 is a schematic illustration of an amplification step of a sandwich assay as known in the art.
Figure 4:
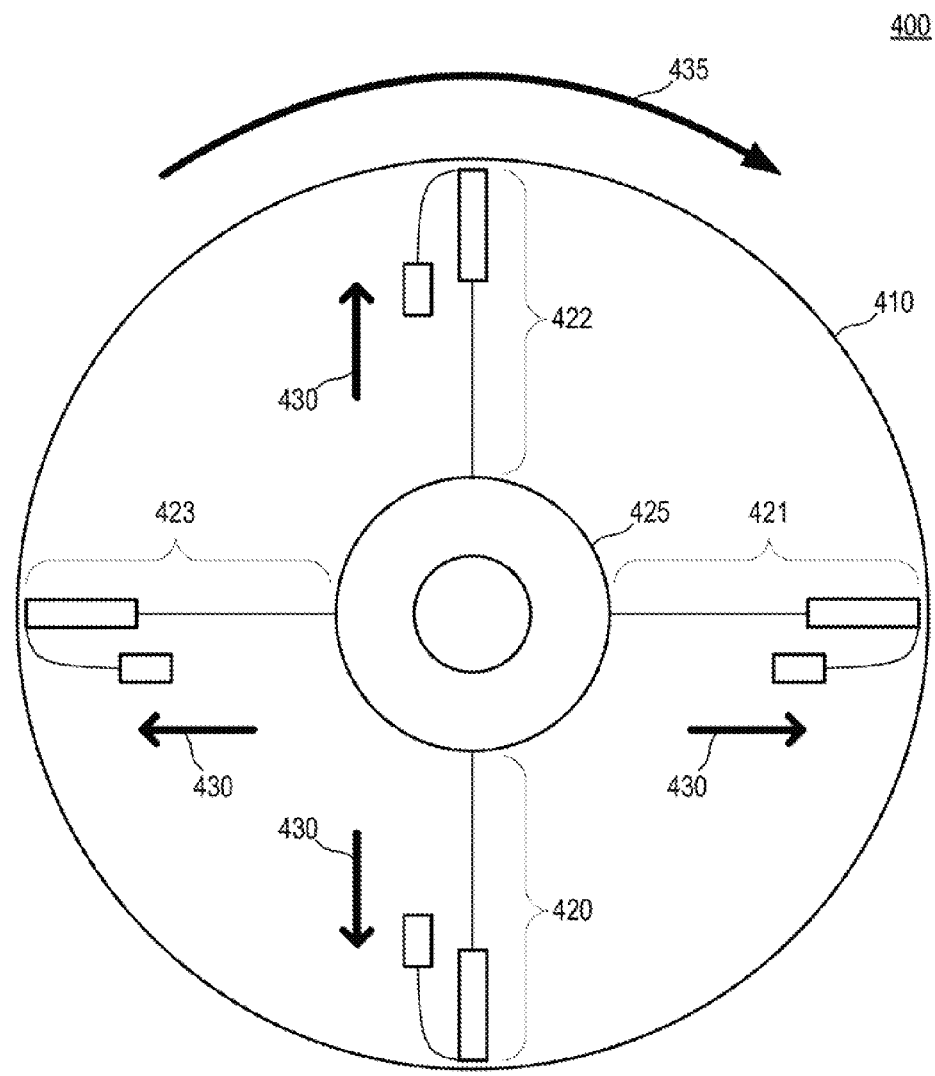
FIG. 4 is a schematic illustration of a microfluidic disk arranged in accordance with embodiments of the present invention.

FIG. 4 is a schematic illustration of a microfluidic disk 400 arranged in accordance with embodiments of the present invention. The microfluidic disk 400 may include a substrate 410 which may at least partially define regions of assay areas 420, 421, 422, and 423. The microfluidic disk 400 may include a fluid inlet port 425 in fluid communication with the assay areas 420, 421, 422, and 423. During operation, as will be described further below, fluids including sample liquids, density media, and/or beads suspended in a fluid, may be transported using centrifugal force from an interior of the microfluidic disk 400 toward a periphery of the microfluidic disk 400 in a direction indicated by an arrow 430. The centrifugal force may be generated by rotating the microfluidic disk 400 in the direction indicated by the arrow 435, or in the opposite direction.

The substrate 410 may be implemented using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the disk 400. In some embodiments, however, opaque plastic, metal or semiconductor substrates may be used. In some embodiments, multiple materials may be used to implement the substrate 410. The substrate 410 may include surface treatments or other coatings, which may in some embodiments enhance compatibility with fluids placed on the substrate 410. In some embodiments surface treatments or other coatings may be provided to control fluid interaction with the substrate 410. While shown as a round disk in FIG. 4, the substrate 410 may take substantially any shape, including square.

In some embodiments, as will be described further below, the substrate 410 may itself be coupled to a motor for rotation. In some embodiments, the substrate may be mounted on another substrate or base for rotation. For example, a microfluidic chip fabricated at least partially in a substrate may be mounted on another substrate for spinning. In some examples, the microfluidic chip may be disposable while the substrate or base it is mounted on may be reusable. In some examples, the entire disc may be disposable. In some examples, a disposable cartridge including one or more microfluidic channels may be inserted into disk or other mechanical rotor that forms part of a detection system.

The substrate 410 may generally, at least partially, define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 µm or less. In some embodiments, the microfluidic features may have a dimension of around 100 µm or less. Other dimensions may be used. The substrate 410 may define one or more fluidic features, including any number of channels, chambers, inlet/outlet ports, or other features.

Microscale fabrication techniques, generally known in the art, may be utilized to fabricate the microfluidic disk 400. The microscale fabrication techniques employed to fabricate the disk 400 may include, for example, embossing, etching, injection molding, surface treatments, photolithography, bonding and other techniques.

A fluid inlet port 425 may be provided to receive a fluid that may be analyzed using the microfluidic disk 400. The fluid inlet port 425 may have generally any configuration, and a fluid sample may enter the fluid inlet port 425 utilizing substantially any fluid transport mechanism, including pipetting, pumping, or capillary action. The fluid inlet port 425 may take substantially any shape. Generally, the fluid inlet port 425 is in fluid communication with at least one assay area 420, and may be in fluid communication with multiple assay areas 420-423 in FIG. 4. Generally, by fluid communication it is meant that a fluid may flow from one area to the other, either freely or using one or more transport forces and/or valves, and with or without flowing through intervening structures.

The assay area 420 will be described further below, and generally may include one or more channels in fluid communication with the fluid inlet port 425. Although four assay areas 420-423 are shown in FIG. 4, generally any number may be present on the microfluidic disk 400.

As the microfluidic disk 400 is rotated in the direction indicated by the arrow 435 (or in the opposite direction), a centrifugal force may be generated. The centrifugal force may generally transport fluid from the inlet port 425 into one or more of the assay areas 420-423.

Figure 5:
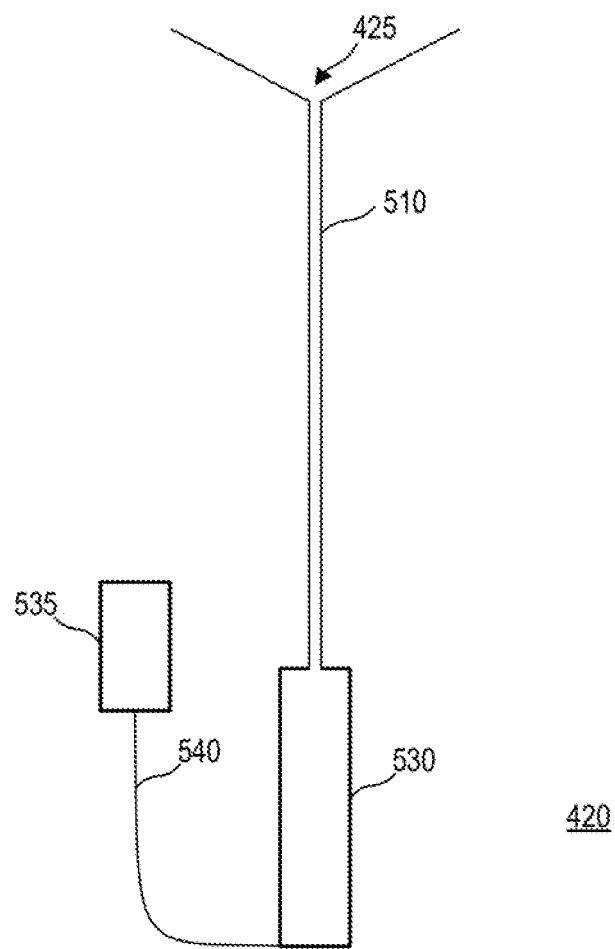
FIG. 5 is a schematic illustration of an assay area of a microfluidic disk in accordance with an embodiment of the present invention.

FIG. 5 is a schematic illustration of an assay area 420 of a microfluidic disk in accordance with an embodiment of the present invention. The assay area 420 includes a channel 510 in fluid communication with the fluid inlet port 425. The channel 510 may be in fluid communication with a detection region 530. Another reservoir 535 may be in fluid communication with the detection region 530 via a channel 540.

The detection region 530 and reservoir 535 may generally be implemented using any size and shape, and may contain one or more reagents including solids and/or fluids which may interact with fluid entering and/or exiting the features.

The reservoir 535 may be configured to contain a density media. The density media is generally a liquid which may have a density lower than a density of beads used in a sandwich assay and higher than a density of the fluid sample. The density media may generally be implemented using a fluid having a density selected to be in the appropriate range—lower than a density of the beads used to conduct a sandwich assay and higher than a density of the fluid sample. In some examples, a fluid sample may be diluted for use with a particular density media. The density media may include, for example, a salt solution containing a suspension of silica particles which may be coated with a biocompatible coating. An example of a suitable density media is Percoll™, available from GE Lifesciences. Particular densities may be achieved by adjusting a percentage of Percoll™ in the salt solution. More generally, viscosity and density may be adjusted by changing a composition of the media. Varying the concentration of solutes such as, but not limited to, sucrose or dextran, in the density media, may adjust the density and/or viscosity of the media. In some embodiments, the density media may include a detergent, such as Tween 20. The detergent may enhance a wash function of transport through the density media, as will be described further below.

The detection region 530 may be a channel or chamber and may vary in configuration in accordance with the detection technique employed, as will be described further below. The detection region 530 may generally be configured to allow for detection of a signal emitted by labeling agents in a complex including a capture agent, target analyte, and labeling agent.

As will be described further below, centrifugal forces may generally be used to transport a fluid sample including beads having capture agents on the surface of the beads from the inlet port 425 toward the detection region 530. Additionally, centrifugal forces may be used to transport density media from the reservoir 535 to the detection region 530.

Figure 6:
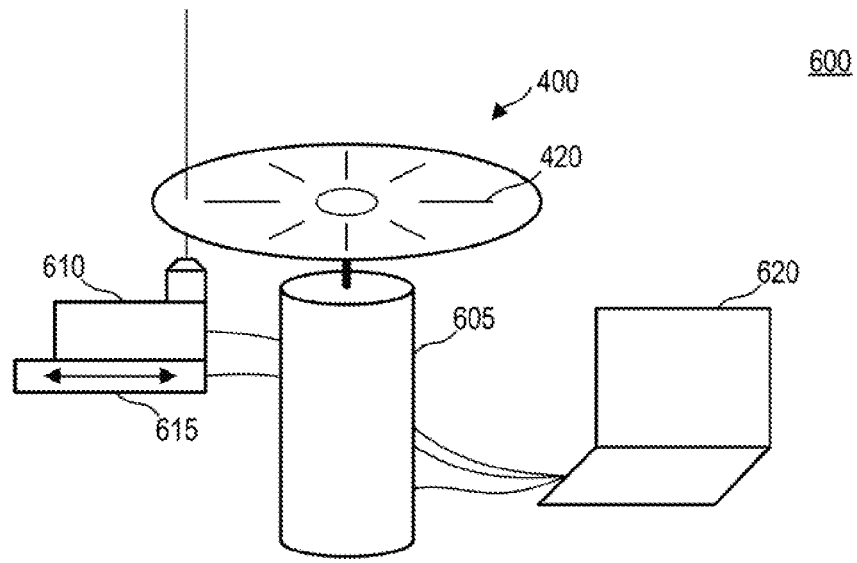
FIG. 6 is a schematic illustration of a system according to an embodiment of the present invention.

FIG. 6 is a schematic illustration of a system according to an embodiment of the present invention. The system 600 may include the disk 400 of FIG. 4 with one or more assay areas 420. A motor 605 may be coupled to the disk 400 and configured to spin the disk 400, generating centrifugal forces. A detection module 610 may be positioned to detect signal from labeling agents in a detection region of the assay area 420, as will be described further below. An actuator 615 may be coupled to the detection module 610 and configured to move the detection module along the detection region in some examples. A processing device 620 may be coupled to the motor 605, the detection module 610, and/or the actuator 615 and may provide control signals to those components. The processing device 620 may further receive electronic signals from the detection module 610 corresponding to the labeling agent signals received by the detection module 610. All or selected components shown in FIG. 6 may be housed in a common housing in some examples. Microfluidic disks, which may be disposable, may be placed on the motor 605 and removed, such that multiple disks may be analyzed by the system 600.

The motor 605 may be implemented using a centrifugation and/or stepper motor. The motor 605 may be positioned relative to the detection module 610 such that, when the disk 400 is situated on the motor 605, the disk is positioned such that a detection region of the assay area 420 is exposed to the detection module 610.

The detection module 610 may include a detector suitable for detecting signal from labeling agents in complexes including at least one capture agent, target analyte, and labeling agent. The complexes may be formed on the surface of one or more beads, as described further below. The detector may include, for example, a laser and optics suitable for optical detection of fluorescence from fluorescent labeling agents. The detection module may include one or more photomultiplier tubes. In other examples, other detectors, such as electronic detectors or CCD cameras, may be used. The actuator 615 may move the detector in some examples where signal may be detected from a variety of locations of the microfluidic disk 400, as will be described further below.

The processing device 620 may include one or more processing units, such as one or more processors. In some examples, the processing device 620 may include a controller, logic circuitry, and/or software for performing functionalities described herein. The processing device 620 may be coupled to one or more memories, input devices, and/or output devices including, but not limited to, disk drives, keyboards, mice, and displays. The processing device may provide control signals to the motor 605 to rotate the disk 400 at selected speeds for selected times, as will be described further below. The processing device may provide control signals to the detection module 610, including one or more detectors and/or actuators, to detect signals from the label moieties and/or move the detector to particular locations, as will be described further below. The processing device may develop these control signals in accordance with input from an operator and/or in accordance with software including instructions encoded in one or more memories, where the instructions, when executed by one or more processing units, may cause the processing device to output a predetermined sequence of control signals. The processing device 620 may receive electronic signals from the detection module 610 indicative of the detected signal from labeling agents. The processing device 620 may detect a target analyte and/or calculate a quantity of a target analyte in a fluid sample based on the signals received from the detection module 610, as will be described further below. Accordingly, the processing device 620 may perform calculations as will be described further below. The calculations may be performed in accordance with software including one or more executable instructions stored on a memory causing the processing device to perform the calculations. Results may be stored in memory, communicated over a network, and/or displayed. It is to be understood that the configuration of the processing device 620 and related components is quite flexible, and any of a variety of computing systems may be used including server systems, desktops, laptops, controllers, and the like.

Having described examples of microfluidic disks and systems in accordance with embodiments of the present invention, methods for conducting sandwich assays will now be described. Some discussion will also be provided regarding mechanisms for sedimentation and centrifugation. The discussion regarding mechanisms is provided as an aid to understanding examples of the present invention, but is in no way intended to limit embodiments of the present invention. That is, embodiments of the present invention may not employ the described mechanisms.

Sedimentation of spheres may occur within a viscous fluid under the influence of a gravitational field (which may be natural or induced by centrifugation). The settling velocity of approximately spherical particles may be described by Stoke's flow equations:

$$V_s = \frac{2}{9} \frac{(\rho_p - \rho_f)}{\mu} g R^2, \qquad \text{(Equation 1)}$$

where $V_s$ is the sedimentation velocity, $\mu$ is the fluid viscosity, $\rho_p$ is the density of the particle, $\rho_f$ is the density of the fluid, g is acceleration due to effective gravity, and R is the particle radius. Note that sedimentation rate scales with the square of particle radius and therefore a small difference in radius may form a basis for separation of particles in some examples, as they may sediment at a different rate. There is also a linear dependence of sedimentation rate with the difference in density between the particle and the surrounding fluid, which may also be an effective mechanism for separation. Accordingly, beads or other particles may be separated according to their density and/or radius based on different sedimentation velocities. Separation of particles using these principles may be referred to as "rate zonal centrifugation."

For nanometer scale particles, such as proteins or nucleic acids, gravitational forces may act in conjunction with Brownian diffusions, but neither will generally cause motion of these nanometer scale particles over significant distances during typical centrifugal conditions (<100,000 g). Accordingly, beads having a surface functionalized by capture agents may be used to separate a target analyte from a fluid sample containing mixture of other small molecules. By forming complexes on the beads, and separating the beads from the remaining sample using centrifugal forces, the need for wash steps may be reduced or eliminated, because unbound labeling agents and/or other molecules may be dissociated from the beads by fluid flow.

Figure 7:
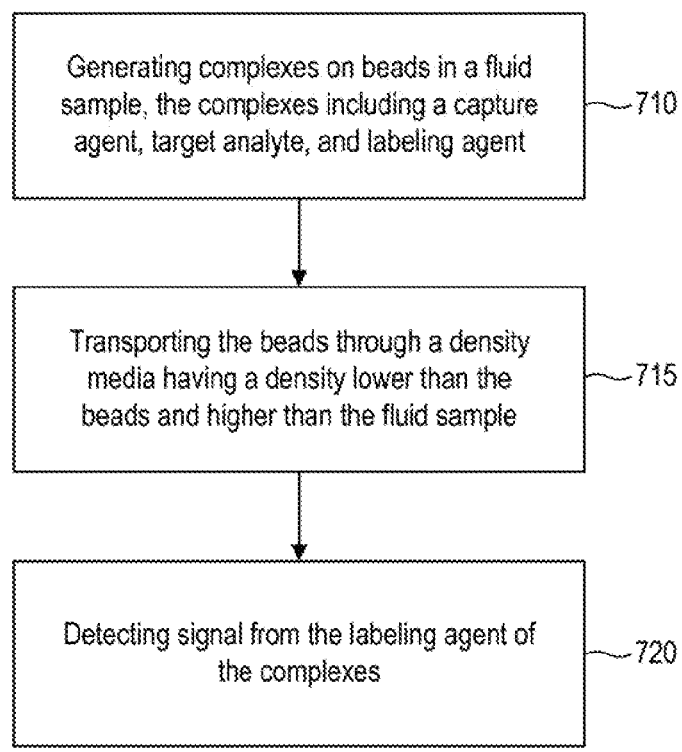
FIG. 7 is a flowchart illustrating a method for conducting a sandwich assay in accordance with an embodiment of the present invention.

FIG. 7 is a flowchart illustrating a method for conducting a sandwich assay in accordance with an embodiment of the present invention. In block 710, complexes may be generated on beads in a fluid sample. The complexes may include a capture agent, target analyte, and labeling agent. Block 710 may be followed by block 715. In block 715, the beads may be transported through a density media having a density lower than the beads but higher than the fluid sample. Gravitational forces, generated naturally or by centrifugation, may be used to transport the beads through the density media. The beads accordingly may sediment out of the fluid sample, forming a concentrated bead pellet. Block 715 may be followed by block 720. In block 720, signal may be detected from the labeling agent of the complexes. In some examples, by separating the beads from the sample fluid using gravitational forces, the beads are also concentrated, which may eliminate or reduce a need for amplification of the labeling agent.

In block 710, complexes including a capture agent, target analyte, and labeling agent may be formed on beads in a fluid sample. Any beads suitable for conducting sandwich assays may be used, including but not limited to, polystyrene beads or silica beads. Substantially any bead radii may be used. Examples of beads may include beads having a radius ranging from 150 nanometers to 3 microns. In other examples, the beads may have a diameter of between 0.15 and 10 microns. Other sizes may also be used. The beads may have a capture agent bound to their surface. The capture agent may be any suitable capture agent for binding to a target analyte. Some specific examples will be provided below, but suitable capture agents include antibodies for binding to one or more proteins, and mRNA probes for binding to DNA and/or RNA in a fluid sample. Similarly, the labeling agent may be any suitable labeling agent for binding to the target analyte and providing a detection signal. Examples include antibodies having a bound fluorescent tag for use in immunoassays and nucleotide probes having a bound fluorescent tag for use in gene expression assays. Fluorescent tags may provide an optical detection signal, however colorimetric or radioactive tags may also be used.

Incubation may take place within a microfluidic disk. Referring back to FIG. 5, a fluid sample containing a target analyte may be introduced to the inlet port 425. Any of a variety of suitable fluid samples may be used including, but not limited to, whole blood, buffer solutions, or other biological fluid samples. Generally, the fluid sample will include target analytes to be detected in accordance with embodiments of the present invention. Any of a variety of target analytes may be detected in accordance with embodiments of the present invention, including proteins, RNA, and/or DNA. The fluid sample may also contain beads having capture agents bound to their surface and/or label agents. In other examples, the beads and/or label agents may be introduced to the fluid sample within the microfluidic disk 400. For example, a fluid containing the beads and/or label agents may be provided to a different inlet port in fluid communication with the channel 510 of FIG. 5. Either by mixing components or by providing a fluid containing the components, a sample fluid including beads having capture agents, target analytes, and labeling agents, may be transported to the detection region 530 of FIG. 5. The transport of the sample fluid may occur through any type of transport mechanism, including centrifugal force, pressure-driven flow, pumping, or other mechanisms. In other examples, beads having capture agents on their surface may be incubated with target analyte and/or labeling agents prior to introduction to a microfluidic disk. In such an example, complexes may be formed on beads in a sample fluid prior to providing the sample fluid to the microfluidic disk.

The detection region 530 of FIG. 5 may contain density media, or density media may be transported into the detection region 530 from another location, such as from the reservoir 535. The channel 540 may have a width selected to serve as a valve, such that a spin rate over a threshold amount is required to initiate a flow of the density media from the reservoir 535 through the channel 540. In some examples, the channel 540 has a width selected such that any spin rates used to transport sample into the detection region 530 are insufficient to transport the density media into the detection region 530. A spin rate of the microfluidic disk 400 may then be increased to initiate or enhance a flow of the density media from the reservoir 535 into the detection region 530. In this manner, the channel 540 may function as a valve. Other valve structures such as wax plugs that melt at a known temperature may be used in other examples.

Accordingly, a sample fluid including: 1) beads having capture agents on their surface; 2) target analytes; and 3) labeling agents may be transported to an interface with a density media. FIG. 8 is a schematic illustration of the detection region 530 containing a sample fluid 805 and a density media 810 in accordance with an embodiment of the present invention. Components of the sample fluid 805 are shown for purposes of illustration beneath the detection region 530 in FIG. 8. The sample fluid includes plurality of beads, including a bead 820 with capture agents 822 on the surface of the beads. The sample fluid 805 further includes target analytes 824 and labeling agents 826.

The sample fluid may then be incubated. FIG. 9 is a schematic illustration of the detection region 530 containing the sample fluid 805 and the density media 810 following an incubation period. Complexes have formed on the bead 820. The target analyte 824 has bound to capture agents 822 and labeling agents 826. Some unbound, free labeling agents 826, however, remain in the sample fluid 805. A time of little to no centrifugal force may be provided to allow for incubation. Additionally, in some examples, a region of the microfluidic disk containing the sample fluid may be heated to enhance incubation. In this manner, complexes may be formed on the beads. As understood in the art, the amount of labeling agent bound to complexes on the beads will generally be proportional to the amount of target analyte in the fluid sample.

The beads may then be transported through the density media. The beads are transported through the density media using centrifugal force, such as that which may be applied by the motor 605 of FIG. 6. Following a period of centrifugal force, the beads may be concentrated in a detection location. FIG. 10 is a schematic illustration of the detection region 530 following transport of beads through the density media. The sample fluid 805 may remain separated from the density media 810, as the density media 810 may have a density higher than that of the sample fluid 805. Free, unbound labeling agent 826, may remain in the sample fluid 805. Beads 820, including complexes, may be transported through the density media 810 to a detection location 830. Beads at the detection location 830 are shown for purposes of illustration under the detection region 530 in FIG. 10. The bead 820 includes complexes containing capture agents 822, target analyte 824, and labeling agent 826. However, unbound labeling agent may not be found in the detection location 830. As shown in FIGS. 8-10, centrifugal force may accordingly be used to separate complexed beads from a sample fluid and to concentrate the complexed beads. In this manner, the need for additional wash and amplification steps in a sandwich assay may be reduced or eliminated. Signal from labeling agent of the concentrated beads may be detected from the detection location 730 using, for example, the detection module 610 of FIG. 6.

In this manner, any of a variety of sandwich assays may be conducted in accordance with embodiments of the present invention, including immunoassays and gene expression assays.

In examples of immunoassays according to embodiments of the present invention, beads coated with an antibody may be mixed with a labeled monoclonal antibody specific for the target analyte and sample of interest. This mixture may be provided to a density media less dense than the beads, but more dense than the fluid sample. If the target analyte is present in the sample, beads may be bound to the labeled antibody through the target analyte. To detect specific antibodies in human serum, beads may be coated with a specific antigen and a secondary antibody against human antibodies may be used as a labeling agent. Following binding of the labeling agent to beads through a target analyte, the beads may be transported through density media, and detected, as generally described above.

In examples of gene expression assays according to embodiments of the present invention, a fluid sample may include prepared cell lysate or may be mixed with cell lysis compounds on the microfluidic disk. For example, referring back to FIG. 5, one or more lysing agents may be provided in fluid communication with the channel 510. The fluid sample may then be mixed with the lysing agents. Beads may be functionalized with capture agents including capture probes complimentary to an mRNA target analyte of interest. Labeling agents may include labeled nucleotides complementary to another segment of the mRNA target analyte of interest. The mixture may be brought to a hybridization temperature, which may be provided by refrigeration and/or heating elements provided on the microfluidic disk 400 of FIGS. 4-5. The refrigeration and/or heating elements may be an integral part of the microfluidic disk 400 or may be in sufficient proximity to the disk to provide temperature control. The hybridization temperature may enhance complex formation. Following complex formation, beads may be transported through the density media and detected as generally described above.

Figure 11:
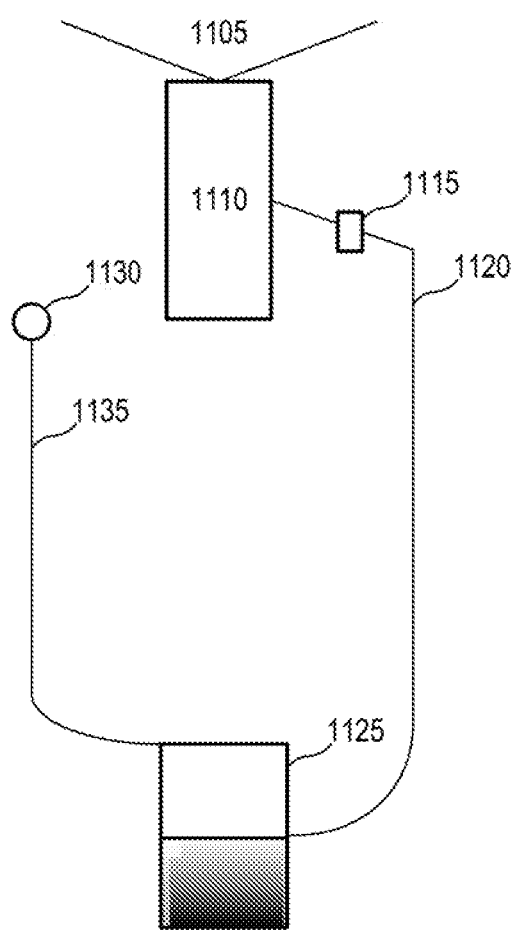
FIG. 11 is a schematic illustration of another example of an assay area according to an embodiment of the present invention.

Any of a variety of sample preparation steps make take place on or off of microfluidic disks prior to transporting beads through density media. FIG. 11 is a schematic illustration of another example of an assay area 420 according to an embodiment of the present invention. An inlet port 1105 is in fluid communication with a sample preparation chamber 1110. The sample preparation chamber is in fluid communication with a channel 1120. A valve 1115 is positioned between the sample preparation chamber 1110 and the channel 1120. The channel 1120 is in fluid communication with a detection region 1125. Another inlet port 1130 is in fluid communication with a channel 1135. The channel 1135 is in fluid communication with the detection region 1125.

The sample preparation chamber 1110, which may take substantially any size and shape, may be used in some embodiments to separate out a portion of the fluid sample prior to transporting the fluid sample toward the detection media. For example, blood cells may be separated from a fluid sample in the sample preparation chamber 1110.

During operation, a whole blood sample including beads for use in a sandwich assay, as generally described above, may be introduced to the inlet port 1105 and sample preparation chamber 1110. The beads may have a diameter less than 1 micron. Blood cells may have diameters ranging from about 6 to 10 microns, and platelets may have a diameter of about 2.5 microns. Accordingly, the microfluidic disk may be spun to separate blood cells and/or platelets to a bottom portion 1112 of the sample preparation chamber 1110. The channel 1120 may intersect the chamber 1110 at a location above where the blood cells and/or platelets have sedimented out of the sample fluid. Due to their small size, most beads may remain suspended in the plasma above the intersection of channel 1120 with the chamber 1110.

The valve 1115 may then be opened, and the disk again spun to transport plasma including suspended beads through the channel 1120. Any of a variety of valves may be used, including a wax valve that may be opened by heating all or a portion of the microfluidic disk 400 to a particular temperature. Other valves may include surface treatment valves, where a portion of the channel 1120 may be treated with a surface treatment impeding flow below a certain force. Other valves may be used.

Density media may be contained in the detection region 1125. The density media may be transported to the detection region from the channel 1135 and inlet port 1130, for example. When the valve 1120 is opened, the plasma including suspended beads may be transported to the detection region 1125, and introduced to the density media. As has generally described above, the beads may then be transported through the density media.

Examples have been described above including methods for conducting a sandwich assay including transporting beads having target analyte complexes through a density media. In some examples, multiple target analytes may be detected in a sample through the use of multiple bead sizes and/or densities. Each bead size may have a surface of capture agents for a different target analyte. The different bead sizes and/or densities may sediment through the density media at different rates, allowing the detection of each bead type. In some examples, following centrifugation, the beads may be stacked at a bottom of a detection region with the largest and/or densest beads at the bottom, and smaller and/or less dense beads layered above.

Briefly, recall sedimentation rate may scale with the square of particle radius. Accordingly, beads of different sizes may be separated from one another by transport through a density media. In some examples, beads may be transported to a bottom or other end of a detection region. Accordingly, in some examples, the bead size differences should be great enough to ensure the largest beads reach the bottom or other end of the detection region before other sized beads. For a sample fluid height of $x_1$, a density media height of $x_2$, and using beads of constant density and constant effective gravity, a recommended difference in bead radius for detectable separation may be given as:

$$\frac{R_1^2}{R_s^2} \geq 1 + \frac{x_1 \mu_1 \Delta \rho_2}{x_2 \mu_2 \Delta \rho_1}; \qquad \text{(Equation 2)}$$

where $R_1$ is the radius of the larger bead, $R_s$ is the radius of the smaller bead, $\mu_1$ is the viscosity of the sample fluid, $\mu_2$ is the viscosity of the density media, $\Delta \rho_1$ is the density differential between beads and the sample fluid and $\Delta \rho_2$ is the density differential between beads and the density media. Note that a similar equation may be derived for beads having a same radius but different densities to yield a minimum recommended density difference between beads used in an multiplex assay. In other examples, both the density and the radius of the beads may be different.

Figure 12:
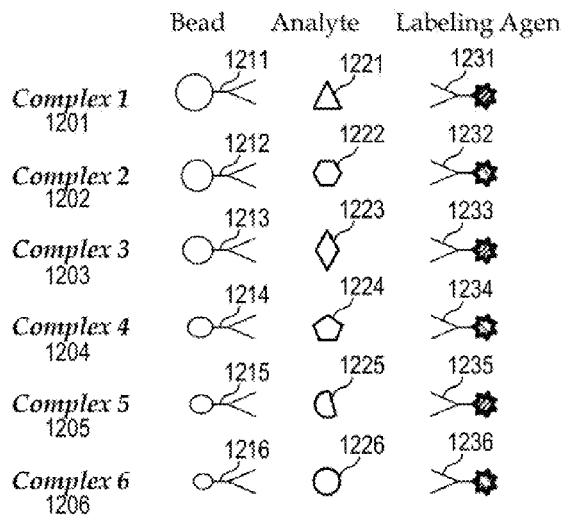
FIG. 12 is a schematic illustration of six complexes that may be formed using different bead sizes according to an embodiment of the present invention.

FIG. 12 is a schematic illustration of six complexes that may be formed using different bead sizes according to an embodiment of the present invention. The complex 1201 includes bead 1211 with a capture agent, target analyte 1221, and labeling agent 1231. The complex 1202 includes bead 1212 with target analyte 1222, and labeling agent 1232. The complex 1203 includes bead 1213 with target analyte 1223, and labeling agent 1233. The complex 1204 includes bead 1214 with target analyte 1224, and labeling agent 1234. The complex 1205 includes bead 1215 with target analyte 1225, and labeling agent 1235. The complex 1206 includes bead 1216 with target analyte 1226, and labeling agent 1236. Each of the beads 1211-1216 has a different radius, and preferably each of the radius' differ by at least the amount described above with reference to equation 2. Alternatively, each of the beads 1211-1216 may have a different density. In other examples, each of the beads 1211-1216 may have some combination of a different density and/or a different radius such that the bead is transported at a different rate through the density media. Although six different beads and associated complexes are shown in FIG. 12, any number may be used including 1, 2, 3, 4, 5, 6, 7, 8, 9, 10, or other numbers of complexes.

Referring back to FIG. 5, during operation, a sample fluid containing each of the beads 1211-1216 may be introduced to the channel 510 and transported to a density media in the detection region 530, such as by spinning the microfluidic disk 400 using the motor 605 of FIG. 6. One or more of the different target analytes 1221-1226 may also be present in the fluid sample, and the labeling agents 1231-1236. As has generally been described above, the complexes 1201-1206 accordingly may form, depending on the presence of the target analytes 1221-1226. The different beads are transported through the density media at different rates, and may form distinct layers in the detection region 530.

Figure 13:
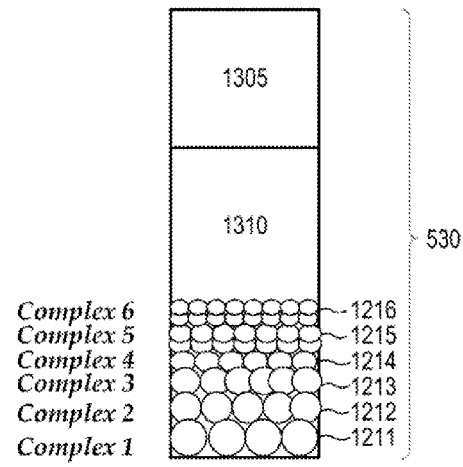
FIG. 13 is a schematic illustration of a detection region following transport of multiple differently sized beads through a density media in accordance with an embodiment of the present invention.

FIG. 13 is a schematic illustration of the detection region 530 following transport of the beads 1211-1216 through a density media. The beads 1211-1216 may be provided in a sample fluid 1305. The sample fluid 1305 may be introduced to a density media 1310. Following transport through the density media 1310, the sample fluid 1305 may remain above the density media 1310, while the beads 1211-1216 may form layers at a detection location of the detection region 530.

A detector may be moved along the detection region 530 to detect any labeling agent bound to any of the beads 1211-1216 through respective target analytes. The distance at which signal may be detected may be indicative of which bead, and which target analyte, was measured. In some examples, the labeling agents of different beads may be selected to further differentiate the signal. For example, referring back to FIG. 12, the labeling agents 1231, 1233, and 1235 may include a red fluorescent tag, while the labeling agents 1232, 1234, and 1235 may include a green fluorescent tag.

Figure 14:
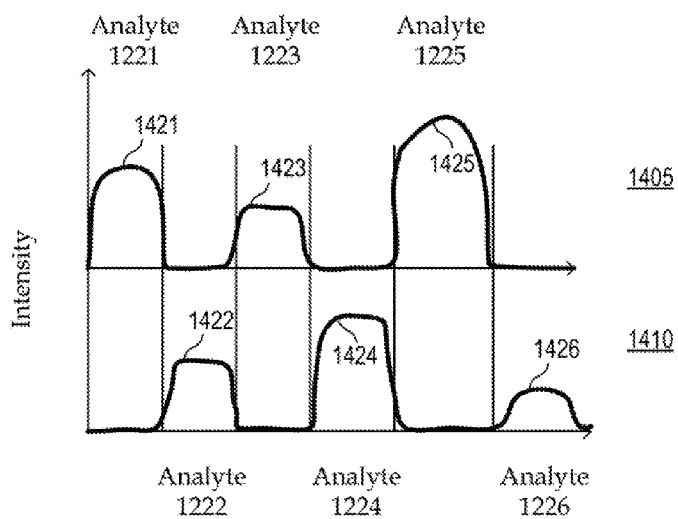
FIG. 14 is a schematic illustration of fluorescent signal detected along a detection region of FIG. 13 in accordance with an embodiment of the present invention.

FIG. 14 is a schematic illustration of fluorescent signal detected along a detection region in accordance with an embodiment of the present invention. Plot 1405 illustrates intensity as a function of distance along the detection region 530 for red fluorescent signal. Plot 1410 illustrates intensity as a function of distance along the detection region 530 for green fluorescent signal. Peaks 1421, 1423, and 1425 correspond to the presence of analytes 1221, 1223, and 1225, respectively. Peaks 1422, 1424, and 1426 correspond to the presence of analytes 1222, 1224, and 1226, respectively.

Accordingly, multiplex assays using beads having different sizes and/or densities may be conducted in accordance with embodiments of the present invention.

One example of an assay using whole blood was described above with reference to FIG. 11. The example described above included separation of blood cells from beads suspended in plasma. In other examples, however, separation of blood cells may not be required as an initial step.

Figure 15:
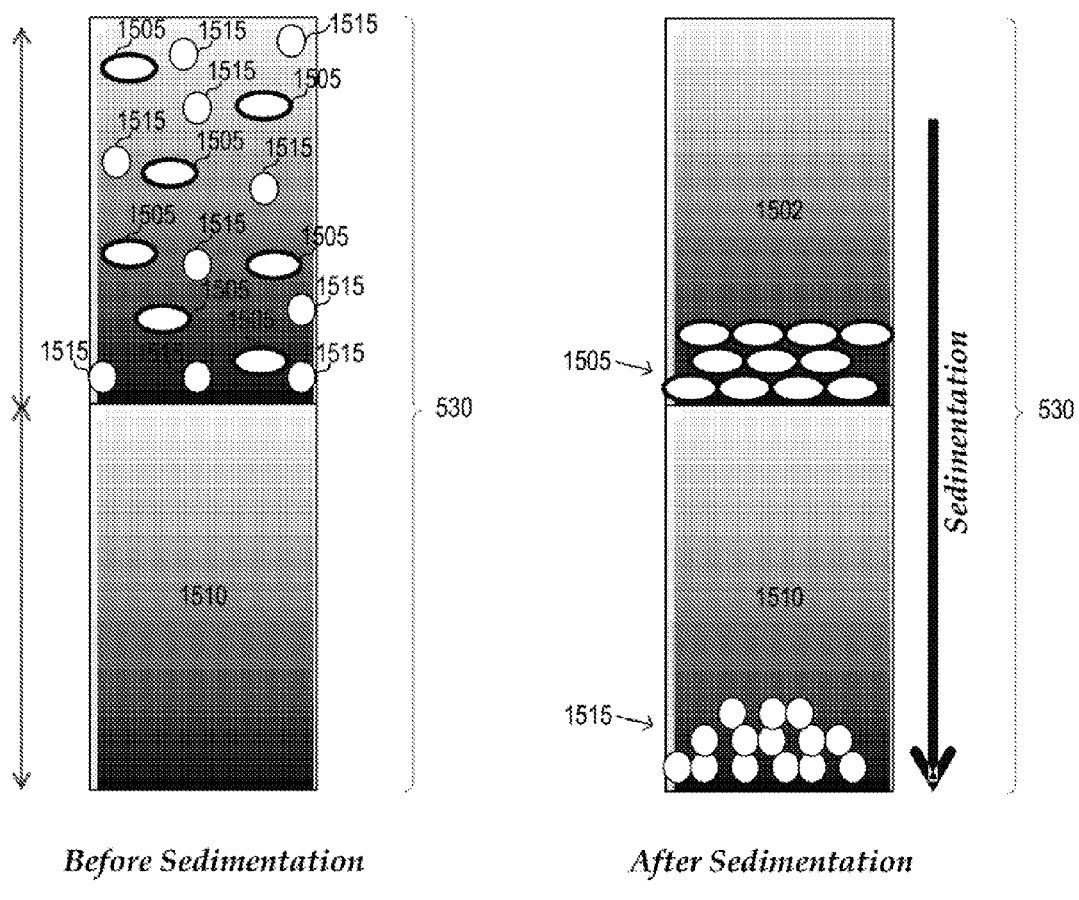
FIG. 15 is a schematic illustration of the detection region of FIG. 5 before and after sedimentation in accordance with an embodiment of the present invention.

FIG. 15 is a schematic illustration of the detection region 530 of FIG. 5 before and after sedimentation in accordance with an embodiment of the present invention. A whole blood sample 1502 including red blood cells 1505 and silica beads 1515 may be introduced to the detection region 530 over a density media 1510. Although not shown in FIG. 15, the silica beads 1515 may include a capture agent on their respective surface configured to bind with target analyte and labeling agent in the fluid sample 1502, as generally described above. The density media 1510 may have a density greater than the red blood cells 1505, but less than that of the silica beads 1515.

Generally, blood cells may have a density less than or equal to 1.095 g/cm$^3$, and the silica beads may have a density of about 2.05 g/cm$^3$. Accordingly, the density media 1510 may have a density of between about 1.095 g/cm$^3$ and 2.05 g/cm$^3$. In one example, the density media 1510 has a density of 1.11 g/cm$^3$.

Sedimentation may occur under the influence of a natural gravitational field, such as by allowing the assay to sit, unpowered, under the influence of a gravitational field. Sedimentation may also occur using centrifugal force, such as by spinning a microfluidic disk. The use of a gravitational field may be preferred over a centrifugal force in embodiments where powered centrifugal force may be undesirable, such as in a pregnancy test. Embodiments of the present invention may accordingly be used to perform a pregnancy test assay using sedimentation. For example, silica beads on the order of 10-30 microns in diameter may sediment in minutes under a normal gravitational field. Following sedimentation, as shown in FIG. 15, the blood cells 1505 may be prohibited from transport through the denser density media 1510. The silica beads 1515, however, may be transported through the density media 1510 to a detection location, and capture analyte may be detected using signal from a labeling agent, as described above.

In some examples, 'beads' as used herein may include one or more biological organisms configured to produce a detectable indicator responsive to the presence of an analyte. The biological organism may include a cell or nematode that produces a detectable indicator responsive to the presence of an analyte. For example, a cell may be used which produces a luminescent product molecule responsive to the presence of a target analyte. An example is the CANARY B-cell based biosensor cell that may be genetically engineered to produce an aequorin protein, which produces light responsive to cellular calcium. In this manner, an assay may be conducted using the biological organism without a need for a separate labeling agent. Rather, the labeling agent may be produced by the biological organism itself responsive to the presence of the analyte. The biological organism may be transported through density media and detected as described herein. In some examples, an enzyme substrate may be included in the density media described herein to enhance or produce signal generation in the biosensor organisms.

EXAMPLES

Experimental examples are provided below for ease in understanding embodiments of the present invention. The examples are not intended to be limiting, nor are the examples intended to be comprehensive.

Example #1

Polystyrene beads coated with antibodies against the bone marrow activation marker Flt-3 ligand and/or the inflammatory cytokine interleukin-6 (IL-6) may be mixed with a sample containing their ligands in the presence of 100 nM second antibody labeled with Alexa 647 (Invitrogen). A microfluidic disk may contain density media including a seven percent dextran dissolved in a physiological salt solution containing 0.05% Tween20. The density of this example density media is 1.025 specific gravity. The microfluidic disk may be spun at 8000 RPM for 10 minutes to introduce the sample containing beads to the density media, and transport the beads through the density media. Fluorescence intensity of the separated beads may be detected by fluorescence microscopy including use of a Cy5 filter and mercury lamp excitation. Average fluorescence intensity may be plotted and displayed and/or stored.

Example #2

Polystyrene beads having a diameter of 1 micron may be coated with IL-6 capture agents and mixed with albumin blocked 1 micron superparamagnetic beads having an iron core and 2.8 micron superparamagnetic beads coated with Fl-3 ligand capture agents in the presence of 100 nM Alexa647 conjugated detection antibodies for each analyte. The mixture may be added to samples containing IL-6 and Fl-3 target analytes in a microfluidic disk. The disk may be spun at 8000 RPM for 10 minutes and the beads may sediment out of solution in order of their density and size, allowing for separate detection of the IL-6 and Fl-3 complexes.

From the foregoing it will be appreciated that, although specific embodiments of the invention have been described herein for purposes of illustration, various modifications may be made without deviating from the spirit and scope of the invention.

What is claimed is:

1. A method of conducting a sandwich assay, the method comprising:
   providing a fluid sample in a channel on a microfluidic disk, the fluid sample comprising a plurality of beads having complexes formed thereon, individual ones of the complexes comprising a capture agent, a target analyte, and a labeling agent, the fluid sample further comprising free labeling agent;
   providing a density media from a media reservoir to a detection region of the microfluidic disk by applying a first centrifugal force, the media reservoir on the microfluidic disk and in fluid communication with the detection region, the detection region fluidly coupled to the channel, wherein the density media has a density within a range, an upper bound of the range being lower than a density of the plurality of beads and a lower bound of the range being higher than a density of the fluid sample;
   spinning the microfluidic disk to apply a second centrifugal force on the plurality of beads, the first and second centrifugal forces being different;
   transporting the plurality of beads including the complexes through the density media, wherein the free labeling agent is restricted from transport through the density media, and wherein a first plurality of beads having a first property is transported to a first distinct detection location and a second plurality of beads having a second property different than the first property is transported to a second distinct detection location;
   detecting a signal from the labeling agents of the complexes; and
   generating an electronic detection signal based, at least in part, on the signal detected from the labeling agents.

2. The method of claim 1, wherein said beads comprise polystyrene beads.

3. The method of claim 1, wherein said beads have a diameter of between 0.15 and 10 microns.

4. The method of claim 1, wherein said beads comprise silica beads.

5. The method of claim 1, wherein said beads comprise biological organisms and said labeling agents are produced by the biological organisms.

6. The method of claim 1, wherein said act of transporting the plurality of beads including the complexes through a density media comprises separating the plurality of beads from free labeling agents in the fluid sample based, at least in part, on different sedimentation rates of the free labeling agents and the plurality of beads.

7. The method of claim 1, wherein the labeling agents comprise fluorescent labeling agents and said transporting the plurality of beads including the complexes through a density media comprises forming a pellet of beads proximal to a detection region, and wherein said detecting comprises detecting fluorescence from said pellet of beads.

8. The method of claim 1, wherein said first plurality of beads have a first radius, and said second plurality of beads have a second radius, and wherein said transporting the plurality of beads including the complexes through a density media comprises transporting the first plurality of beads to a first location and the second plurality of beads to a second location based, at least in part, on a sedimentation rate of said first and second plurality of beads, and wherein said detecting comprises detecting signal from the first plurality of beads at said first location and detecting signal from the second plurality of beads at said second location.

9. The method of claim 1, wherein said first plurality of beads have a first density, and said second plurality of beads have a second density, and wherein said transporting the plurality of beads including the complexes through a density media comprises transporting the first plurality of beads to a first location and the second plurality of beads to a second location based, at least in part, on a sedimentation rate of said first and second plurality of beads, and wherein said detecting comprises detecting signal from the first plurality of beads at said first location and detecting signal from the second plurality of beads at said second location.

10. The method of claim 1, wherein said capture agent and said labeling agent comprise antibodies, and wherein said target analyte comprises a protein.

11. The method of claim 1, wherein said capture agent and said labeling agent comprise nucleotide probes for mRNA, and said target analyte comprises mRNA.

12. The method of claim 1, wherein said fluid sample comprises whole blood, and the method further comprises:
   separating red blood cells from the plurality of beads using sedimentation at least in part prior to said transporting the plurality of beads including the complexes through a density media.

13. An apparatus for conducting a sandwich assay, the apparatus comprising:
   a substrate, wherein the substrate at least in part defines a channel;
   a fluid sample contained in the channel, wherein the fluid sample includes a plurality of beads having complexes formed thereon, individual ones of the complexes comprising a capture agent, a target analyte, and a labeling agent, wherein the fluid sample further includes free labeling agent;
- a detection region coupled to the channel and defined at least in part by the substrate;
- a media reservoir defined at least in part by the substrate and in fluid communication with the detection region, the apparatus operable to transport a density media from the media reservoir to the detection region responsive to a first centrifugal force, wherein the density media has a density within a range, an upper bound of the range being lower than a density of the plurality of beads and a lower bound of the range being higher than a density of the fluid sample; and
- wherein the channel is in fluid communication with the detection region such that the plurality of beads in the fluid sample are transported from the channel through the density media responsive to a second centrifugal force different than the first centrifugal force, and wherein at least a portion of the free labeling agent is restricted from transport through the density media, and wherein the plurality of beads comprise a first plurality of beads having a first property and a second plurality of beads having a second property, different than the first property such that the first plurality of beads are transported to a first distinct detection location and the second plurality of beads are transported to a second distinct detection location.

14. The apparatus of claim 13, wherein the substrate comprises a disc.

15. The apparatus of claim 13, further comprising a separation chamber defined in part by the substrate and in fluid communication with the channel, the apparatus further comprising:
- a valve coupled between at least a portion of the channel and the separation chamber.

16. The apparatus of claim 13, wherein the property comprises radius and the first plurality of beads have a first radius and the second plurality of beads have a second radius.

17. The apparatus of claim 13, wherein the property comprises density and the first plurality of beads have a first density and the second plurality of beads have a second density.

18. A system for conducting a sandwich assay, the system comprising:
- a microfluidic disk comprising:
  - a substrate, wherein the substrate at least in part defines a channel;
  - a fluid sample contained in the channel, wherein the fluid sample includes a plurality of beads having complexes formed thereon, individual ones of the complexes comprising a capture agent, a target analyte, and a labeling agent, wherein the fluid sample further includes free labeling agent;
  - density media disposed in a reservoir in the microfluidic disk, wherein the density media has a density higher than a density of the fluid sample and lower than a density of the plurality of beads;
  - a detection region coupled to the channel and defined at least in part by the substrate; and
  - wherein the reservoir is coupled to the detection region such that the density media flows into the detection region responsive to a first centrifugal force and wherein the channel and detection region are coupled such that the plurality of beads in the fluid sample are transported from the channel through the density media responsive to a second centrifugal force, different from the first centrifugal force, and wherein at least a portion of the free labeling agent is restricted from transport through the density media;
- a motor coupled to the microfluidic disk, the motor configured to receive a motor control signal and spin the microfluidic disk responsive to the motor control signal;
- a detection module positioned to detect a signal from label agents included in the complexes, wherein the detection module is configured to generate an electronic detection signal based, at least in part, on the signal from the label agents; and
- a processing device coupled to the motor and the detection module, wherein the processing device is configured to generate the motor control signal and provide the motor control signal to the motor, and wherein the processing device is further configured to receive the electronic detection signal from the detection module.

19. The system of claim 18, wherein the signal from the label agents comprises an optical signal and wherein the detection module comprises a laser and photomultiplier.

20. The system of claim 19, wherein the detection module further comprises an actuator coupled to the laser and the processing device, and wherein the actuator is configured to move the laser along the detection region responsive to an actuator control signal received from the processing device.

21. The system of claim 19, wherein the processing device is further configured to calculate a quantity of target analyte in the fluid sample based, at least in part, on the electronic detection signal.

22. The system of claim 21, wherein the processing device is configured to integrate at least a portion of the electronic detection signal over time to calculate the quantity of target analyte in the fluid sample.

* * * * *